United States Patent
Thomson et al.

(10) Patent No.: US 6,800,282 B1
(45) Date of Patent: Oct. 5, 2004

(54) CELL CULTURE PRODUCTS

(75) Inventors: Brian Mark Thomson, Pocklington (GB); Saad Abdul Majeed Ali, York (GB); Nicholas Medcalf, Pocklington (GB); John Maltman, Clifton (GB); Sharon Dawn Maltman, Clifton (GB)

(73) Assignee: Smith & Nephew, Plc, London (GB)

( * ) Notice: Subject to any disclaimer, the term of this patent is extended or adjusted under 35 U.S.C. 154(b) by 0 days.

(21) Appl. No.: 09/446,379

(22) PCT Filed: Jun. 26, 1998

(86) PCT No.: PCT/GB98/01882

§ 371 (c)(1),
(2), (4) Date: Feb. 11, 2000

(87) PCT Pub. No.: WO99/00151

PCT Pub. Date: Jan. 7, 1999

(30) Foreign Application Priority Data

Jun. 26, 1997 (GB) .............................................. 9713406
Nov. 28, 1997 (GB) .............................................. 9725209

(51) Int. Cl.$^7$ .............................. C12N 5/00; A61K 9/70
(52) U.S. Cl. ...................................... 424/93.7; 424/445
(58) Field of Search ................................ 424/445, 443, 424/400, 93.7

(56) References Cited

U.S. PATENT DOCUMENTS 5,599,788 A * 2/1997 Purchio et al.

FOREIGN PATENT DOCUMENTS

| WO | WO-9309176 A2 | * | 5/1993 |
| WO | WO-9706835 A1 | * | 2/1997 |
| WO | WO-9706837 A1 | * | 2/1997 |

* cited by examiner

Primary Examiner—Jean C. Witz
(74) Attorney, Agent, or Firm—Stites & Harbison PLLC; B. Aaron Schulman

(57) ABSTRACT

A wound dressing which comprises a carrier layer having a non-adherent to cell layer on a wound facing surface thereof. The non-adherent layer has bonded thereto a biodegradable cell anchoring layer which anchors mammalian cells. In use, the degradable layer breaks down releasing the cells into the wound site which are discouraged from reattaching to the dressing by the non-adherent layer. Thus the dressing can switch from a cell binding state to a state in which the binding of cells is discouraged. Systems, methods of treatment and methods of manufacturing the dressing are also disclosed.

17 Claims, 11 Drawing Sheets

CELL CULTURE PRODUCTS

The present invention relates to the culturing of mammalian anchorage dependent cells onto a carrier substrate. More particularly, the present invention relates to wound dressings suitable for treating e.g. partial thickness wounds such as burns or skin graft donor site and to systems for the preparation of such dressings.

The current widely practised approach to the treatment of severe skin trauma necessitates the removal of dead tissue which might otherwise support the proliferation of pathogenic micro-organisms. However, this procedure often leaves massive open wounds which require closure and the use of autologous skin grafts is not particularly desired for a number of reasons, not least because there may be, in cases of serious burns for example, a limited supply of unaffected tissue. Cadaver skin grafts have been used to temporarily close a wound site but its limited supply and the perceived concern with cross-contamination with bacterial or viral pathogens has led to a search for alternatives.

In recent years, techniques for the in vitro cultivation of keratinocytes from human epidermis have been developed for culturing on epidermal sheets to cover full thickness burns. In the earliest versions of this approach, a confluent usually mutilayered keratinocyte sheet was grown on tissue culture plastic in vitro. The cell layer would then be detached from the culture plastic using degradative enzymes, inverted and placed upon the wound. Reports on the efficiency of this approach indicate that substantial practical difficulties exist (see, for example, J Bum Care Rehab. 13, 174–180).

More recently keratinocytes have been cultured on flexible, biocompatible membranes to facilitate the transfer of cell sheets onto the wound site. See for example, our patent application WO91/13638. Other illustrative examples of this approach include those disclosed in WO88/08448, EP 0364306, EP 0387975 and U.S. Pat. No. 5,266,480. One difficulty with prior art approaches is that the use of membranes optimised for keratinocyte attachment thereto during the culturing phase can often inhibit the migration of the cells from the membrane onto the wound, following the application of the wound dressing. Indeed, the prior art has tended to concentrate on improving the attachment of cells to the membrane, see for example U.S. Pat. No. 5,558,861 where the use of microbially produced cellulose is disclosed having an animal cell adhesive protein physically or chemically bonded thereto, the express aim of which is to provide a cellulose gel having an excellent adhesion to epidermal cells.

It is therefore an object of the present invention to provide a wound dressing which comprises a carrier layer that promotes the culturing and anchoring of anchorage dependent cells in vtro thereto yet following application to a wound, the dressing becomes substantially non-adherent to cells.

In accordance therefore with the present invention provides a wound dressing comprising a carrier layer having a wound-facing surface, said surface being non-adherent to anchorage-dependent cells and having disposed thereon a biodegradable cell anchoring layer.

By the term "biodegradable cell anchoring layer" we mean a layer, capable of anchoring cells thereto, that is susceptible to degradation or breakdown following application of the dressing to the wound.

It is preferred that the dressing is conformable i.e the dressing will conform to changes in contours of the body portion to which the dressing is applied.

In preferred embodiments the carrier layer is in the form of a gel, e.g. hydrogel, a film or sheet. A film is particularly preferred. Films suitable as the carrier layer may be continuous or apertured e.g formed into a net. The film may be flat or contoured. The contours may be produced for example by embossing. Suitably contoured films may also have apertures.

The carrier layer may comprise a material which is inherently non-adherent to cells or alternatively the material may be surface treated e.g coated, with a non-adherent to cell material, to provide a carrier layer having a non-adherent to cell wound facing surface. It is observed that when a material is non-adherent to cells, the cells when suspended in a suitable aqueous medium in contact with the non-adherent material appear rounded up and do not attach to the material. In contrast, where a material is adherent to cells, the cells will attach to the material and "sit down". Furthermore, the cells will resist detachment when washed gently with physiological compatible saline.

Useful materials that are non-adherent to cells include cross-linked cellulose derivatives. Preferred examples thereof include cross-linked hydroxyalkyl celluloses e.g. hydroxyethyl cellulose, hydroxypropyl cellulose, methyl, thyl and methyl thyl celluloses (available from Sigma Co and Aldrich). Cross-linked carboxyalkyl celluloses are also preferred e.g. carboxymethyl cellulose (CMC, available from Hercules Ltd, Lancashire, UK) cross-linked with ethylene glycol diglycidyl ether (EGDGE) or 1,4 butanediol diglycidyl ether. Other preferred materials include polyvinyl alcohol (PVA, Sigma Co), Cell-Form™ (ICN), agarose e.g Sepharose™.

Alternatively a material which is adherent to cells maybe surface treated e.g by coating or by chemical/physical bonding with a non-adherent to cell material so as to provide a carrier layer having a non-adherent to cell wound facing surface. Illustrative examples of adherent materials employed in the present invention include polymers, particularly synthetic polymers, such as those disclosed in our patent applications WO 91/13638 and WO 97/06835. Apt polymers therefore include polyhydroxyethylmethacrylic acid (polyHEMA), cross linked polyvinylalcohol (PVA), polyacrylic acid cross linked with triallylsucrose (Carbopol), polyvinylpyrrolidone, polyetherpolyesters, polyetherpolyamides, polyacrylamides and polyethylene oxide and polyurethanes. Other apt polymers include copolymers such as those containing vinyl acetate residues such as ethylenevinyl acetate copolymers. Suitable ethylene-vinyl acetate copolymers are those containing not more than 20% vinyl acetate. A preferred material, known as EVA 538/539 contains 16% vinyl acetate. Other suitable polymers include essentially hydrocarbon based materials such as polybutadienes, polypropylene and polystyrene. Further examples include block copolymers having hard end blocks and softer mid blocks. Apt block copolymers include stryene based rubbers such as styrene-butadiene styene (manufactured under the trade name CARIFLEX or KRATON, Shell chemical Co). The adherent mat rial may then be coated on the wound facing surface with phosphoichloline, or silicone, polyethylene glycol or polytetrafluroethylen (PTFE).

The carrier layer may comprise a material which is biodegradable or non-biodegradable following application of the dressing to the wound site. Illustrative examples of biodegradable materials include photopolymerizable hydrogels such as those disclosed in U.S. Pat. No. 5,410,016, incorporated herein by reference, and sold under the trade name FOCAL (Focal Inc, USA).

The carrier layer may also comprise a backing layer disposed on a non-wound facing surface to increase the robustness of the wound dressing. Accordingly, the wound dressing may comprise a carrier layer in the form of a laminate film comprising a carrier layer described hereinbefore having a backing layer disposed on a non wound-facing surface. The backing layer may be fabricated from imaterials commonly used in the manufacture of wound dressings such as polypropylene, polyurethanes, polyesters and polyethylene. Particular preferred are polyurethanes. Preferred polyurethane backing layers include cyclic polyether polyurethanes, ESTANE 5714™ (BF Goodrich) OPSITE IV3000™ hydrophilic polyurethane film (Smith & Nephew). Polyurethane backing layers may be chemically modified with treatments such as plasma treatment with nitrogen, ammonia or air, corona discharge treatment or flame treatment to increase the surface energy of the surface of the backing layer which contacts the non wound facing surface. This aims to enhance the weftability of the backing layer and thereby improve the interface between the backing layer and non wound facing surface.

It is preferred that the carrier layer is sterilised by any suitable known methods of sterilisation. Suitable forms of sterilisation include ethylene oxide (allowing the required time for degassing), gamma-irradiation or steam sterilisation.

It is preferred that the carrier layer is permeable to wound exudate so as to prevent the build-up of exudate under the wound dressing which might lead to the lifting or arching of the dressing away from the wound site and therefore reducing the effective contact area of the dressing with the wound site.

This permeability may be achieved by rendering the carrier layer sufficiently porous to wound exudate. Such rendering is standard practice in the art. Suitably, the carrier layer is permeable to moisture vapour, oxygen and carbon dioxide. In this way a dressing when in place on the wound will provide moist conditions allowing for the cells to remain viable while the wound heals and prevent the accumulation of wound exudate. It is preferred that the wound dressing of the present invention has a minimum moisture vapour transmission rate (MVTR) of around 250 to 300 g/m$^2$.

The biodegradable cell anchoring layer preferably anchors the cells through attaching to the carrier layer an animal cell adhesion protein, the protein being capable of anchoring cells. According to this approach, the cell anchoring layer preferably comprises a natural or synthetic polyanion. Preferred natural polyanions include heparans, for example. heparin, heparin sulphate, fucoidin, (available from Sigma Co) syndecan, betaglycan and perlecan. Other preferred natural polyanions include inositol phosphates e.g. inositol hexaphosphate, dextran sulphate, pentosan and mesoglycans (available from Sigma Co). A synthetic polyanion such as polyvinyl sulphate (available from Sigma Co) may be used.

The polyanion is preferably cross-linked to bind the polyanion to the carrier layer. This may be achieved by the addition of an effective amount of a cross-linking agent e.g. EGDGE. It is preferred that a polyanion is utilised due to its non-specific binding properties with respect to animal cell adhesion proteins. That is, polyanions are capable of binding a large variety of animal cell adhesion proteins. As a result, the cell anchoring layer having a variety of animal cell adhesion proteins attached thereon is capable of anchoring more cells since it increases the probability that the cells will be expressing at least one factor capable of being anchored to at least one type of animal cell adhesion protein. Furthermore, polyanions bind growth factors, e.g. epidermal cell growth factors for example fibroblast growth factor (FGF). Therefore, advantageously, this promotes the formation of an engraftable cell layer. A source of cell adhesion proteins comprising a multitude of different cell adhesion proteins is preferred. Foetal calf serum (FCS) is a preferred source. Alternative sources to FCS include defined and recombinantly derived protein mixtures.

Preferably, to form the biodegradable anchoring layer, the polyanion is first made up into aqueous solution and maybe either spread on or sprayed onto the non-adherent to cell layer and allowed to dry. The polyanion may then be cross-linked as described hereinbefore.

Alternatively the cell anchoring layer may anchor the cells 'directly', that is, without the use of adhesion proteins. Short specific peptides e.g. RGD, YIGSR (available from Sigma Co) may be grafted onto non-adherent to cell layer. Other protein and peptides such as those found in soya protein may be used.

Alternatively, a polycationic peptide may anchor the cell directly. An example of which is polylysine (Sigma Co). An advantage of these direct methods is that they obviate the need to use adhesion proteins, particularly those derived from bovine sources, which would come into contact with a wound during use of the dressing.

The cells of the present invention are preferably mammalian epithelial or mesenchymal cells e.g. keratinocytes or fibroblasts (including precursors thereto). Melanocytes in co-culture with keratinocytes may also be used. It is preferred for burn and chronic wounds that keratinocytes are used. Preferably the keratinocytes are autologous cells, harvested according to standard techniques of the art.

Alternatively, a mixture of autologous and allogenic cells could be utilised with the present invention. In particular, where the main clinical concern is rapid closure of a dermal wound, a wound dressing according to the present invention comprising e.g. 90% allogenic keratinocytes and 10% autologous keratinocytes may be provided. The aim of which is to produce rapid wound closure following the application of the dressing. Following which, the autologous cells will progressively repopulate the wound site as the allogenic cells are rejected.

In a further alternative embodiment, the wound dressing of the present invention may comprise a mixture of keratinocytes and fibroblasts. It has been shown that the addition of fibroblasts to keratinocyte cultures markedly increases the production of basement membrane components. Such an effect may be usefully exploited to overcome the known weakness in the dermal-epidermal junction observed with current epidermal grafts.

Thus in accordance with another aspect of the present invention, we provide a wound dressing comprising;
  (a) a carrier layer having a wound facing non-adherent to cells surface having disposed thereon a biodegradable cell anchoring layer;
  (b) a layer of mammalian cells anchored to the cell anchoring layer.

The wound dressing of the present invention may be used in the treatment of a variety of wounds. The dressing of the invention is particularly suitable for treating partial thickness wound e.g. where the epidermis and possibly only part of the dermis is lost. Such wounds include skin graft donor sites, first or second degree burns, leg ulcers or pressure sores. The dressing may also be used for venous ulcers. In addition, the dressing of the present invention may find further use as part of a treatment for the chronic skin wounds that may develop following tumour excision and radiotherapy.

The wound dressing of the present invention maybe used in conjunction, e.g. simultaneously or sequentially, with other treatments, for example, dermal replacement products such as D rmagraft (Trademark).

Thus in accordance with the present invention, we further provide a method of treating a skin trauma site on a mammalian patient comprising the step of;

applying to a patient a wound dressing which dressing comprises (a) a carrier layer having a wound-facing non-adherent to anchorage dependent cells surface and having disposed thereon a biodegradable cell anchoring layer;

(b) a layer of mammalian cells anchored to the anchoring layer.

The wound dressing of the present invention may be prepared in accordance with standard cell culture techniques. The dressing may be placed in a suitable, preferably transparent, culture vessel with the cell anchoring layer face up. The vessel may be formed from suitable materials conventionally used in the manufacture of tissue culture vessels. High impact polystyrene is preferred. The dressing is then submerged in an aqueous medium comprising the cells and, if appropriate, the cell adhesion proteins. The medium utilised may be those commonly used in the field, e.g. dulbecco's modified eagle's medium (DMEM). The medium further comprises the usual nutrients, e.g. glucose, nonessential amino acids etc. Sufficient time is elapsed to allow the cells to become anchored to the cell anchoring layer and form a preferably sub-confluent layer.

It is preferred, however, to pretreat the carrier layer of the present invention e.g. by washing, with a solution of adhesion proteins such as FCS and then placing the dressing in a culture vessel comprising the aqueous media which includes nutrients, $O_2$ etc. and the cells. This accelerates the attachment of the cells by providing the cells with a ready-made layer i.e. the cell anchoring layer, on which to be anchored.

The dressing may then be removed from the culture vessel and applied to the wound of a patient, bringing the cell layer into contact with the wound site. The dressing may then be secured to the patient and left in place on the wound. Over a period of time, the cell anchoring layer which is suitably susceptible to enzymatic breakdown by e.g. proteases and heparinase present in the wound site, will degrade or breakdown, releasing the cell layer anchored thereto into the wound site. The non-adherent to cell layer disposed on the wound facing surface discourages re-attachment of the cells to wound dressing.

If clinical concern dictates, proteases or heparinases may be added by the physician to the dressing once in place to accelerate the release of the cell layer.

In accordance with a further aspect of the present invention, we provide a method of preparing a wound dressing comprising the steps of;

(a) forming a surface which is non-adherent to anchorage dependent cells on a wound facing surface of a carrier layer;

(b) forming a biodegradable cell anchoring layer on a non-adherent to anchorage dependent cells surface of a carrier layer;

(c) culturing a carrier layer and biodegradable cell anchoring layer in the presence of mammalian cells.

The advantages of the wound dressing of the present invention include the ability to transfer cells from the dressing to the wound site more rapidly than with prior art devices. This is particularly desirable when rapid wound closure is desired. In use, the degradable layer breaks down releasing the cells into the wound site which are discouraged from attaching to the wound facing surface of the dressing by the non-adherent layer. The breakdown of the degradable layer will be further promoted by the presence degradative enzymes known to be present in certain wound types. Thus the dressing can 'switch' from a cell binding state to a state in which the binding of cells to the dressing is discouraged.

The invention will now be illustrated by way of example only and with reference to the accompanying figures in which.

Figure 3A:
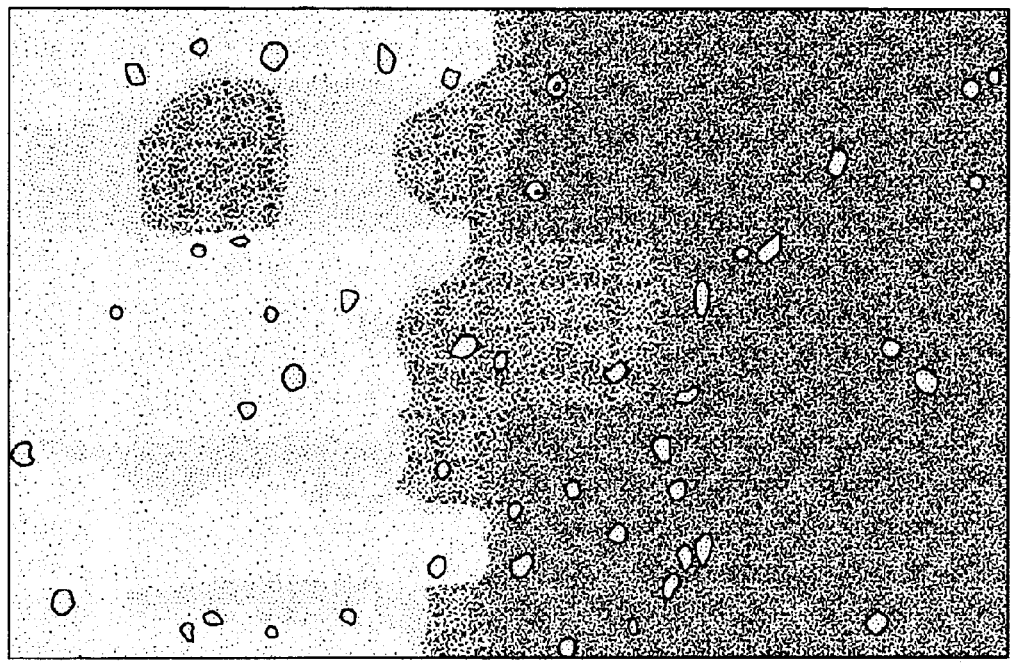
Figure 3B:
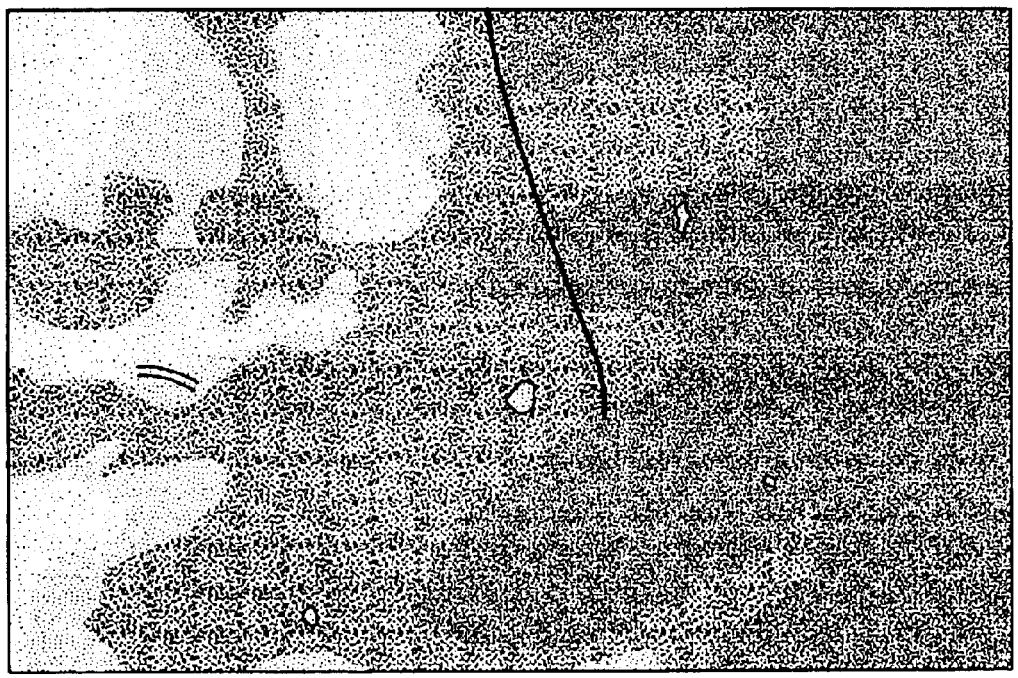
Figure 3C:
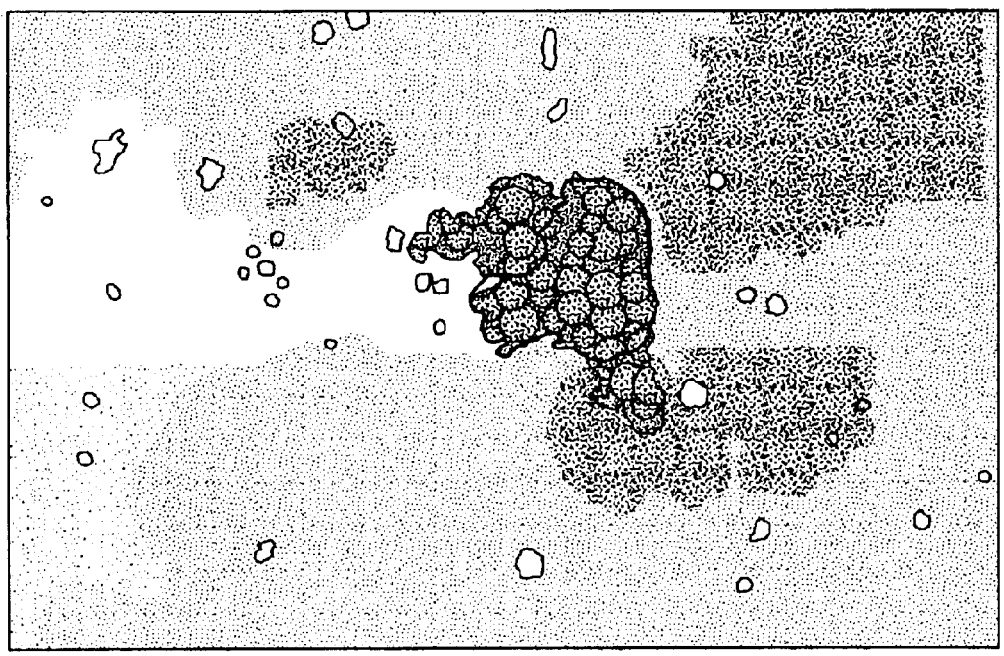
Figure 3D:
Figure 3E:
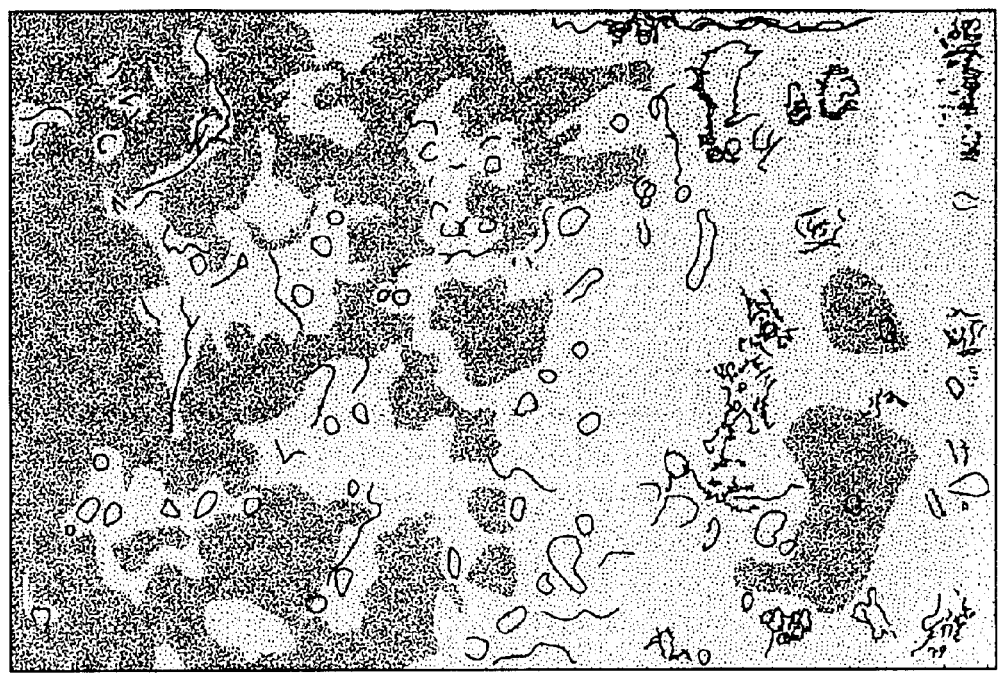

FIGS. 3a to e illustrate photomicrographs of the views of FIG. 1a to e respectively after 16 hours from application of the cells to the film. FIG. 3c demonstrates that the cells remain non-adherent and form tighter clumps with increasing time. In contrast, FIG. 3e demonstrates the spreading of adherent Scaber cells upon the FCS pre-treated CMC/heparin films.

Figure 1A:
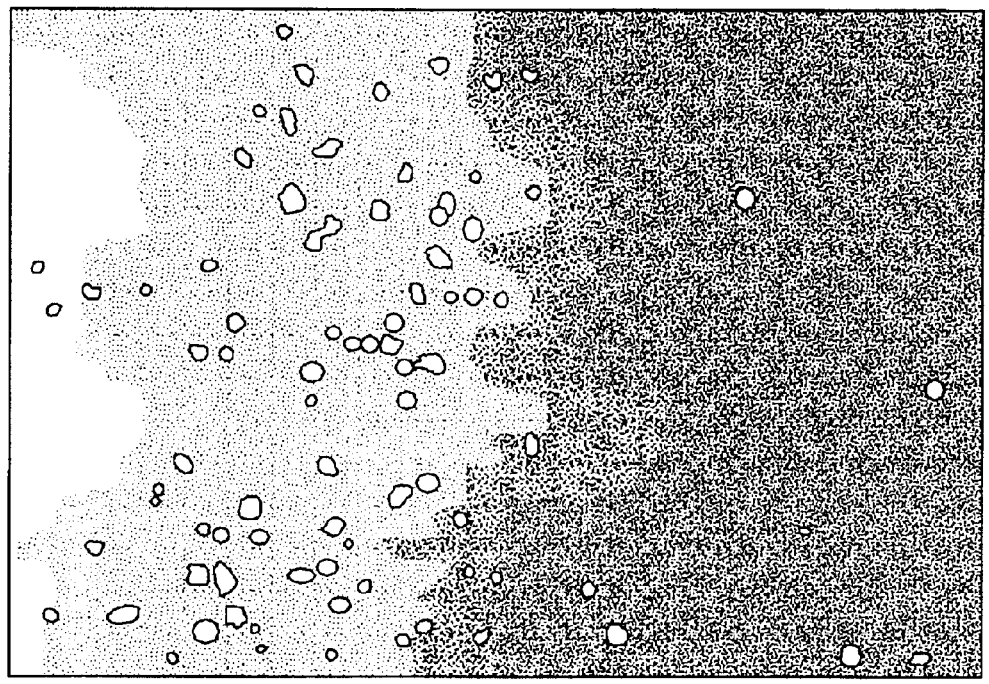
FIG. 1a illustrates a photomicrograph of Scaber keratinocytes cells adhering to tissue culture plastic after four hours in culture.
Figure 1B:
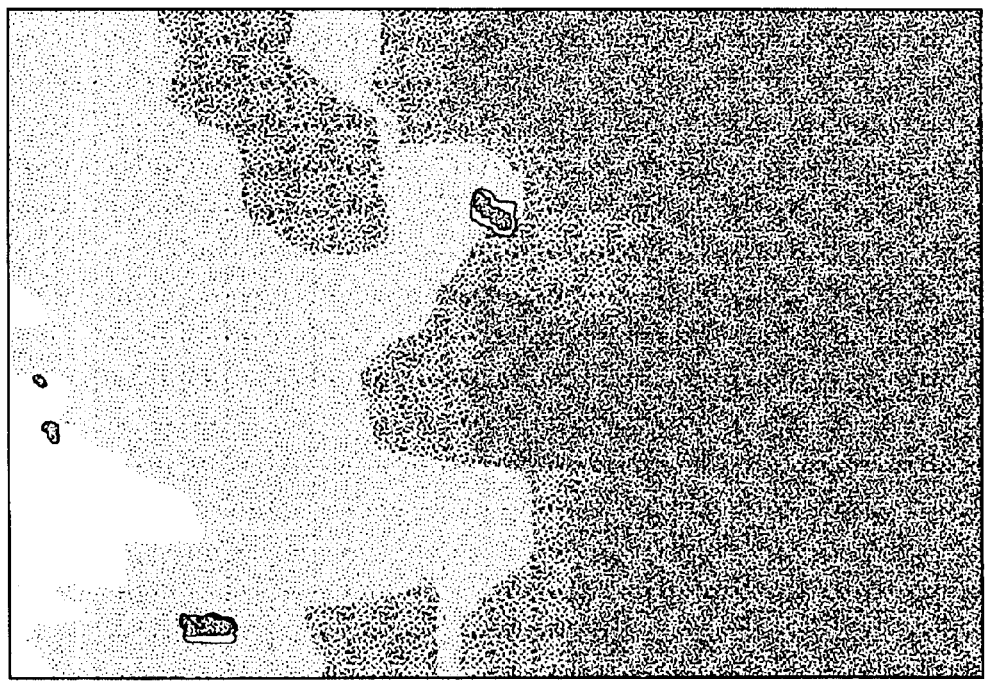
FIG. 1b illustrates photomicrograph of FCS pre-treated CMC films prepared as in example 1 below but without the addition of heparin.
Figure 1C:
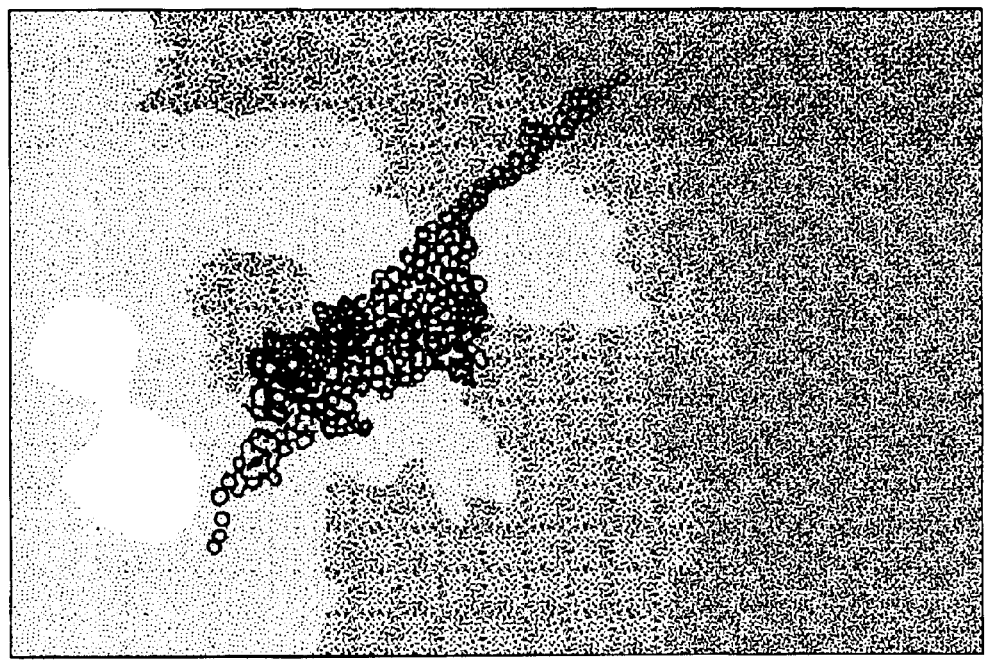
FIG. 1c illustrates a photomicrograph of Scaber cells cultured on the films of FIG. 1b demonstrating that the cells do not adhere to the film and instead adhere to each other.
Figure 1D:
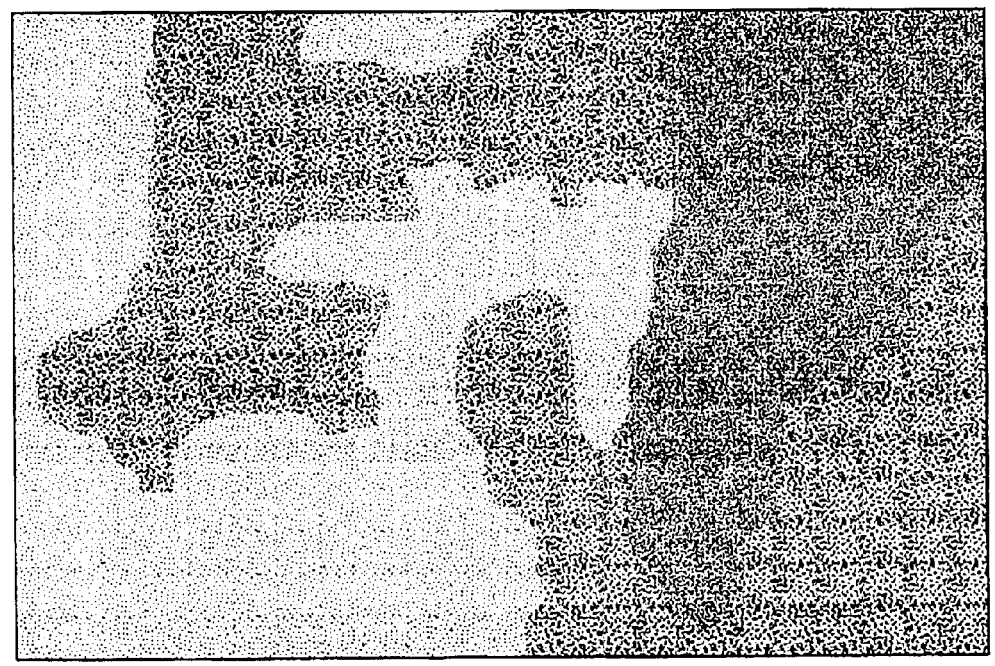
FIG. 1d illustrates a photomicrograph of FCS pre-treated CMC/heparin films without cells prepared in accordance with example 1 below.
Figure 1E:
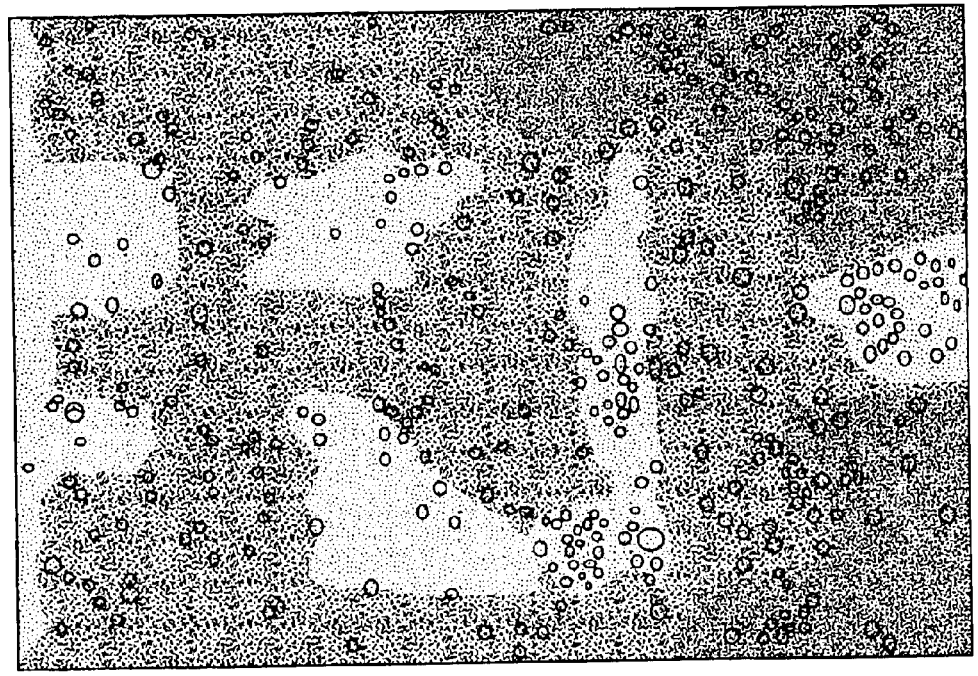
FIG. 1e illustrates photomicrograph Scaber cells on the films of FIG. 1d and demonstrating that the cells begin to adhere within 4 hours.
Figure 2A:
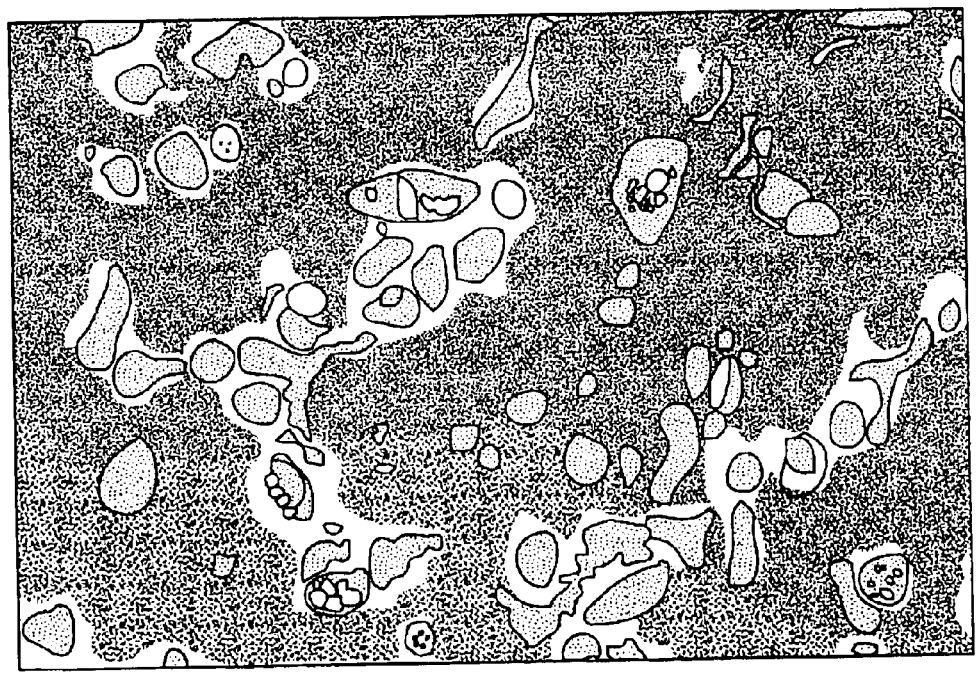
FIG. 2a illustrates a higher magnification photomicrograph view of FIG. 1a (mag×100)
Figure 2B:
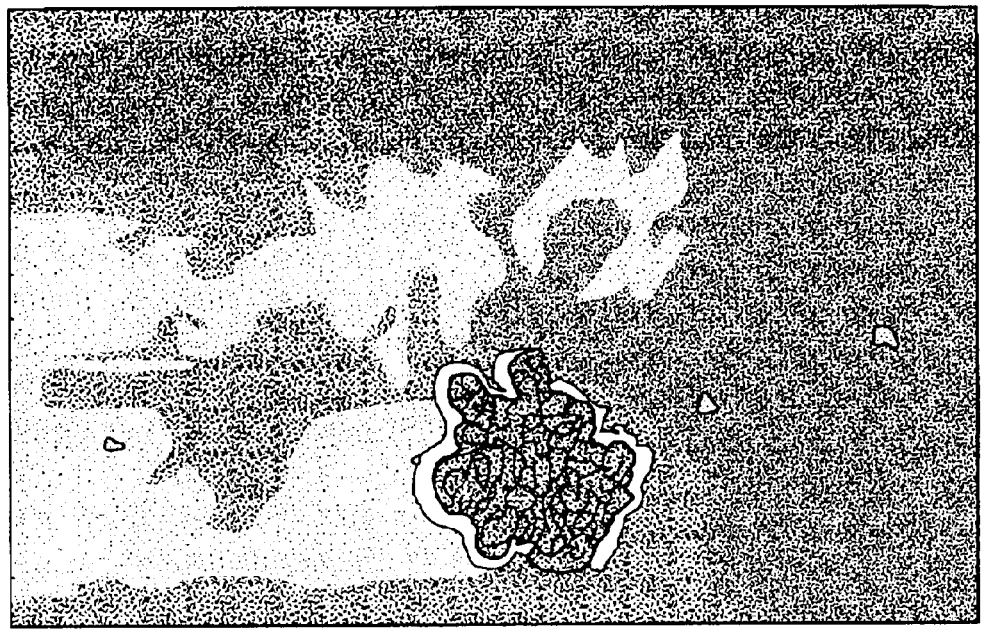
FIG. 2b illustrates a high magnification photomicrograph view of FIG. 1c (mag×100) demonstrating that the cells remain non-adherent and begin to dump.
Figure 2C:
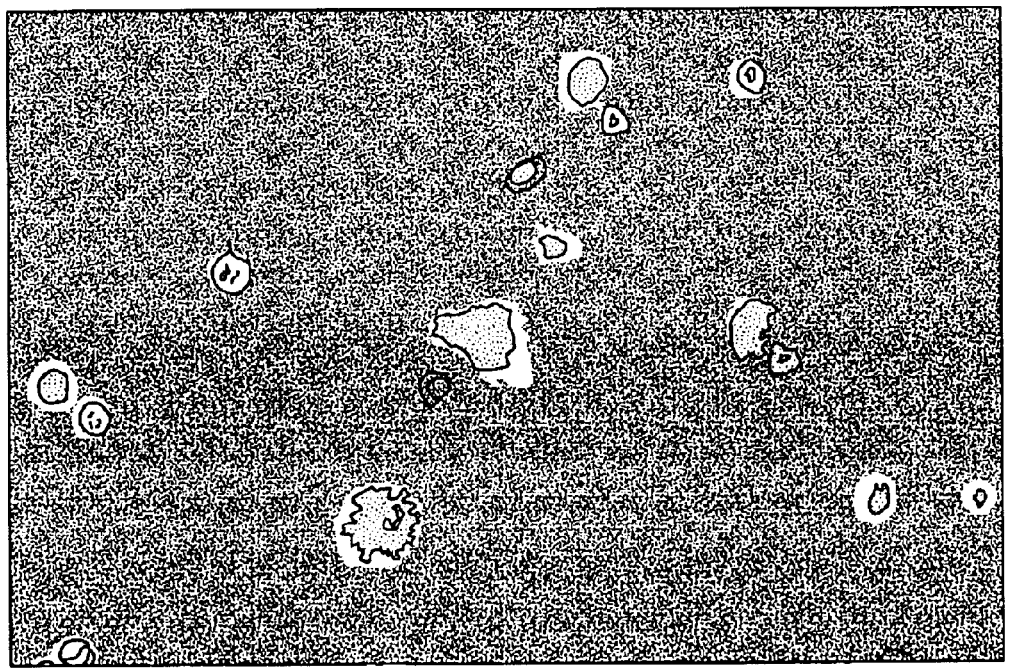
FIG. 2c illustrates a high magnification view of FIG. 1e (mag×100), demonstrating the spreading of the applied cells over the film.
Figure 4A:
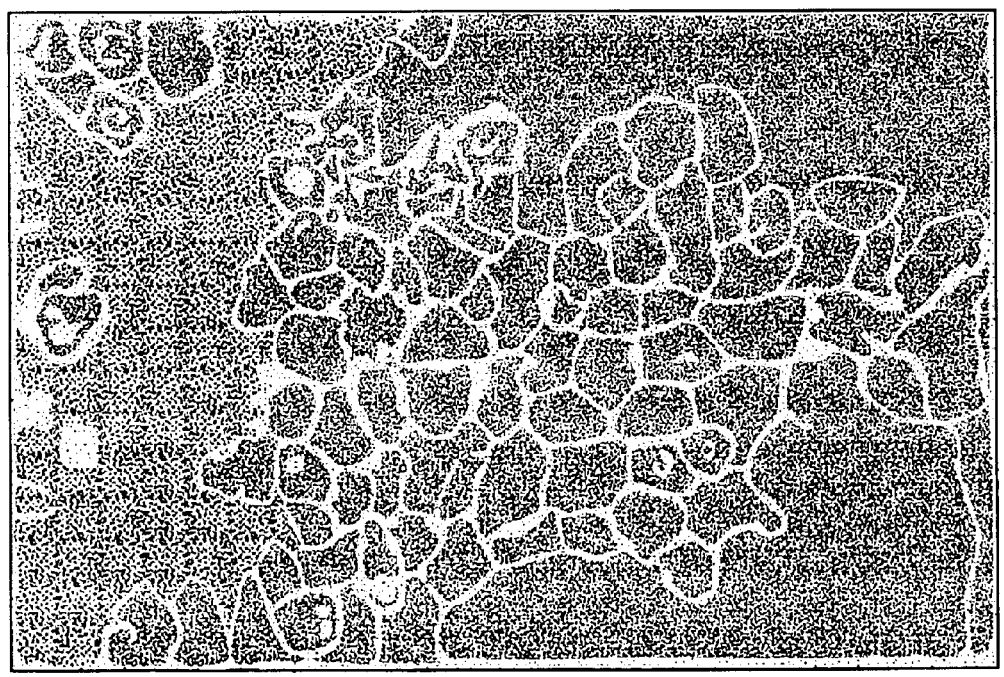
Figure 4B:
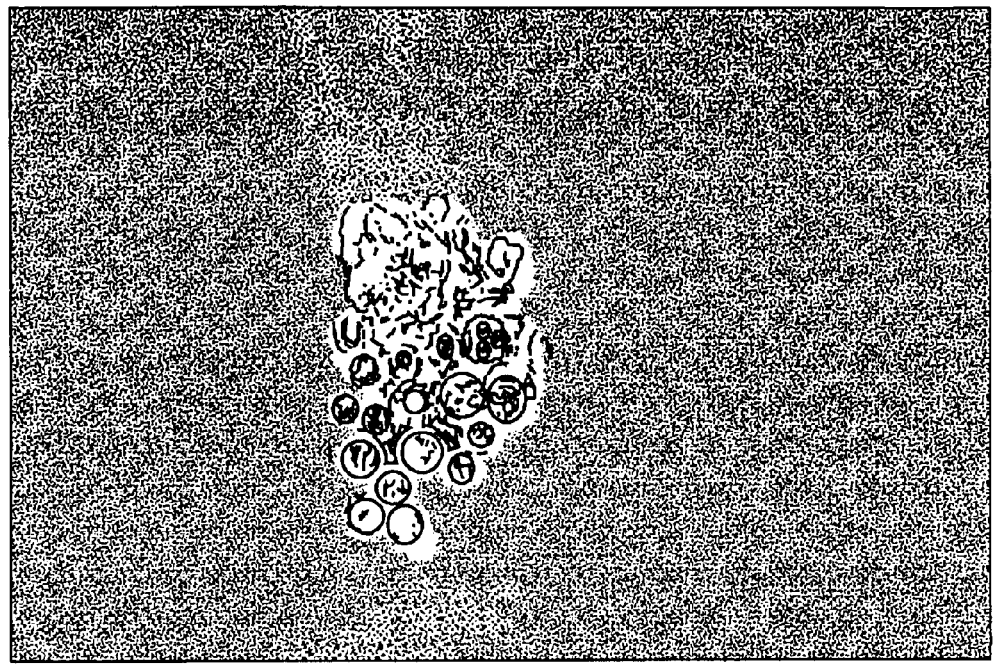
Figure 4C:
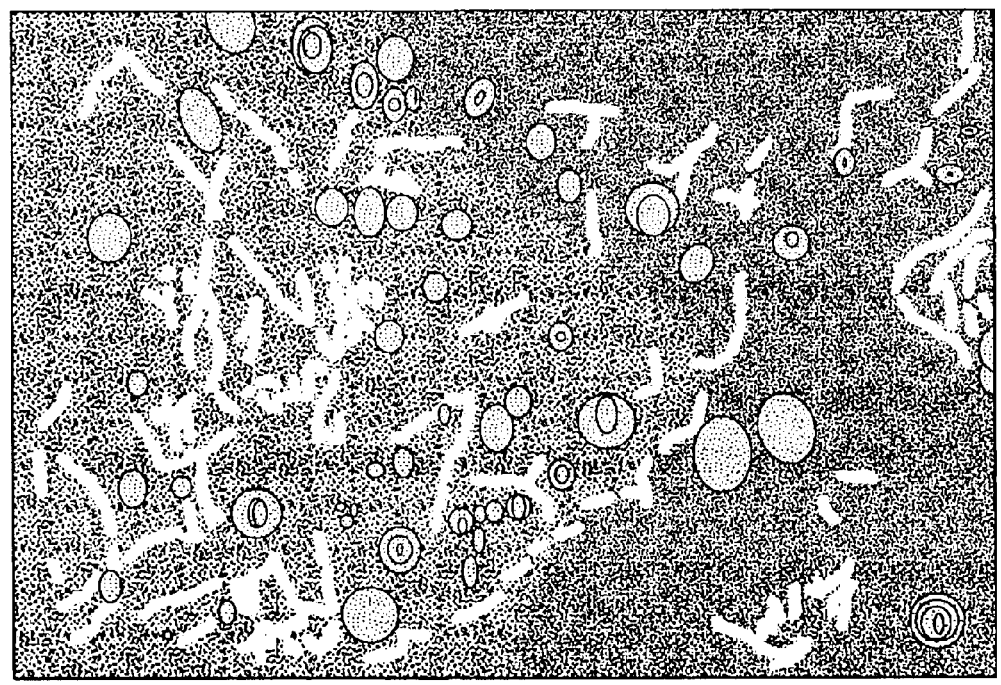

FIG. 4 illustrates a photomicrograph of the view of FIG. 2a to c after 16 hours from the application of cells to the film.

Figure 5A:
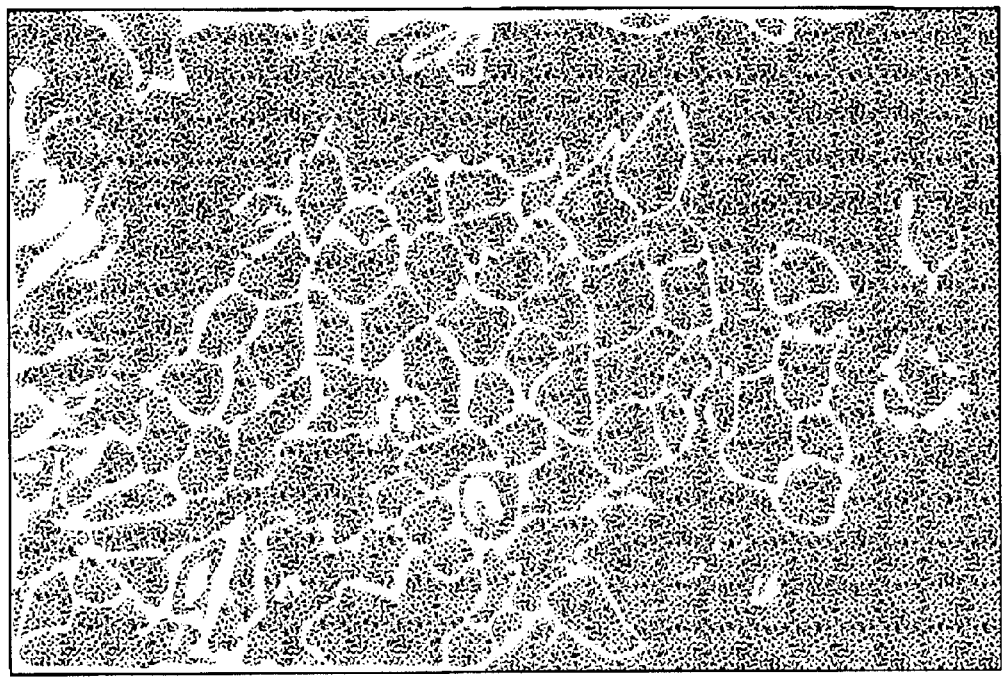

FIG. 5a illustrates a photomicrograph of Scaber cells grown upon tissue culture plastic for 7 days. The cells remain adherent.

Figure 5B:
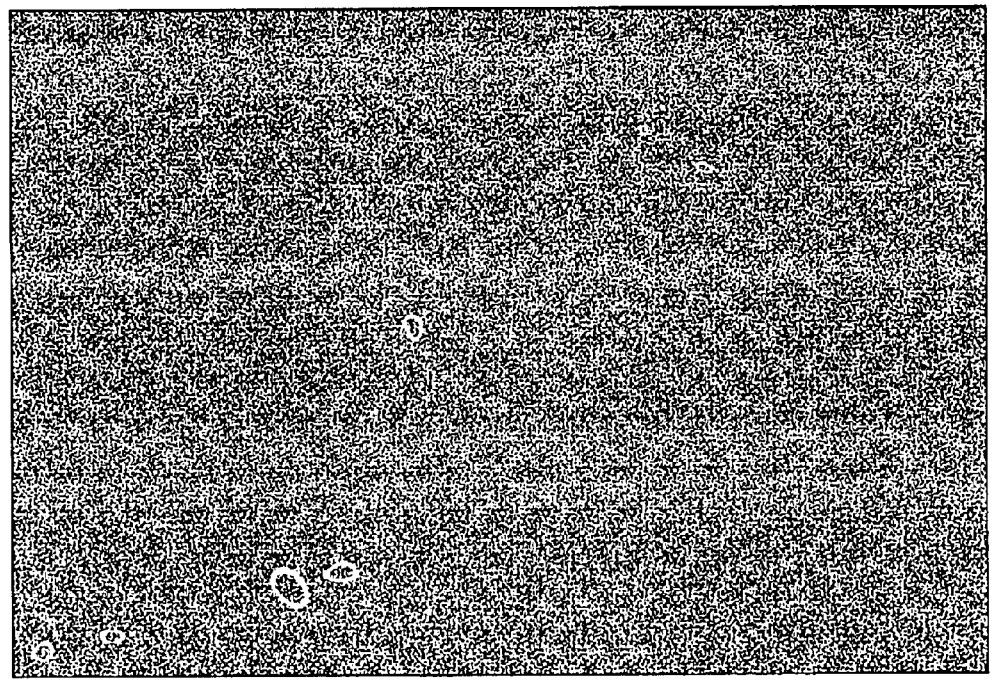

FIG. 5b illustrates a photomicrograph of FCS pre-treated CMC films without cells for 7 days.

Figure 5C:
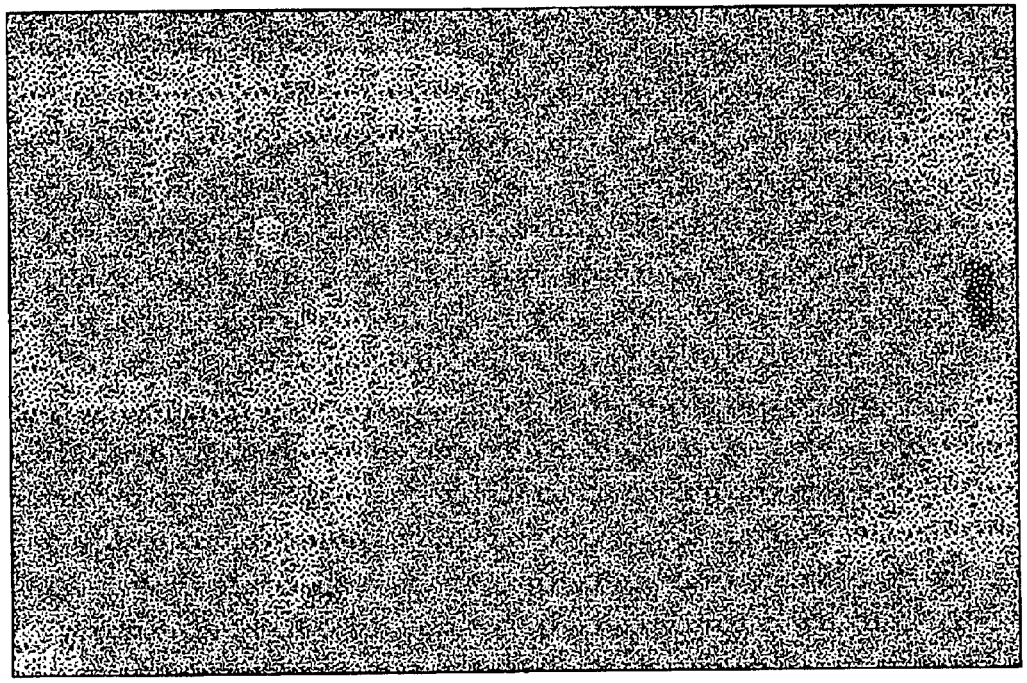

FIG. 5c illustrates a photomicrograph of cell seeded, FCS pretreated CMC films after 7 days, demonstrating the absence of adherent cells.

Figure 5D:
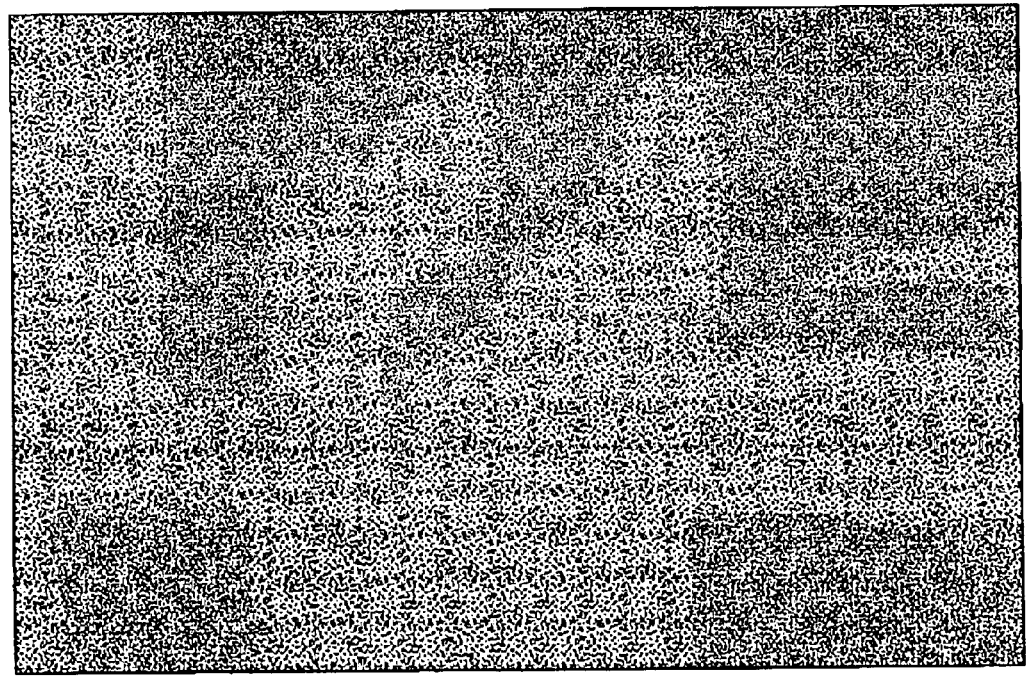
Figure 5E:
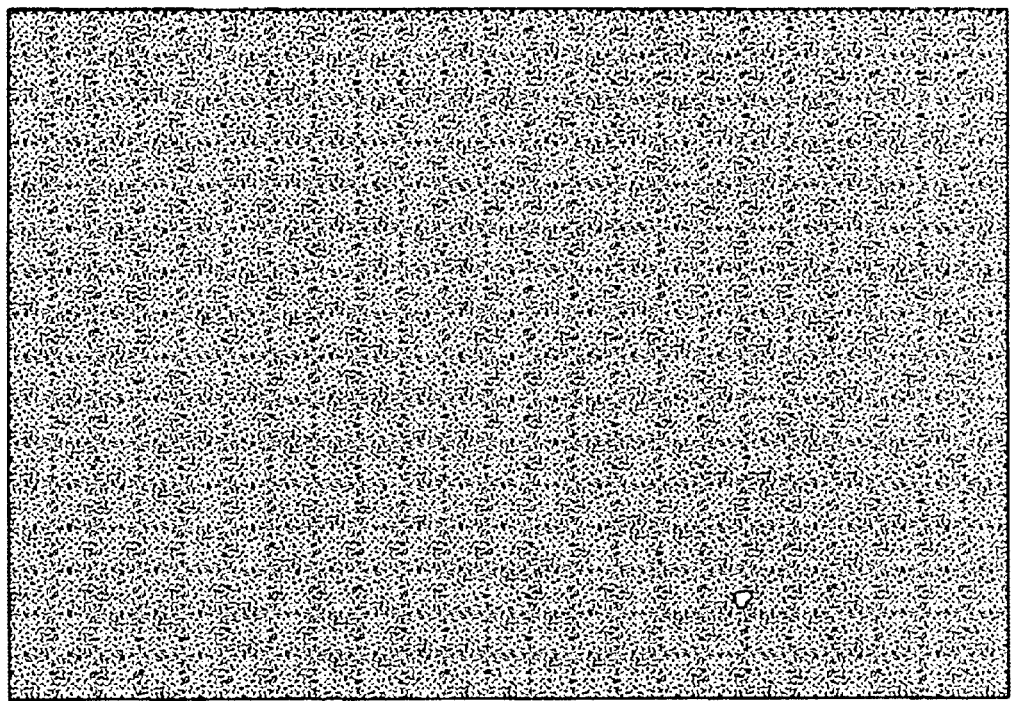

FIG. 5d illustrates a photomicrograph of FCS pre-treated CMC/heparin films incubated without cells for 7 days FIG. 5e illustrates a photomicrograph of cell seeded FCS pre treated CMC/heparin films after 7 days demonstrating that the adherent cells have detached.

Figure 6:
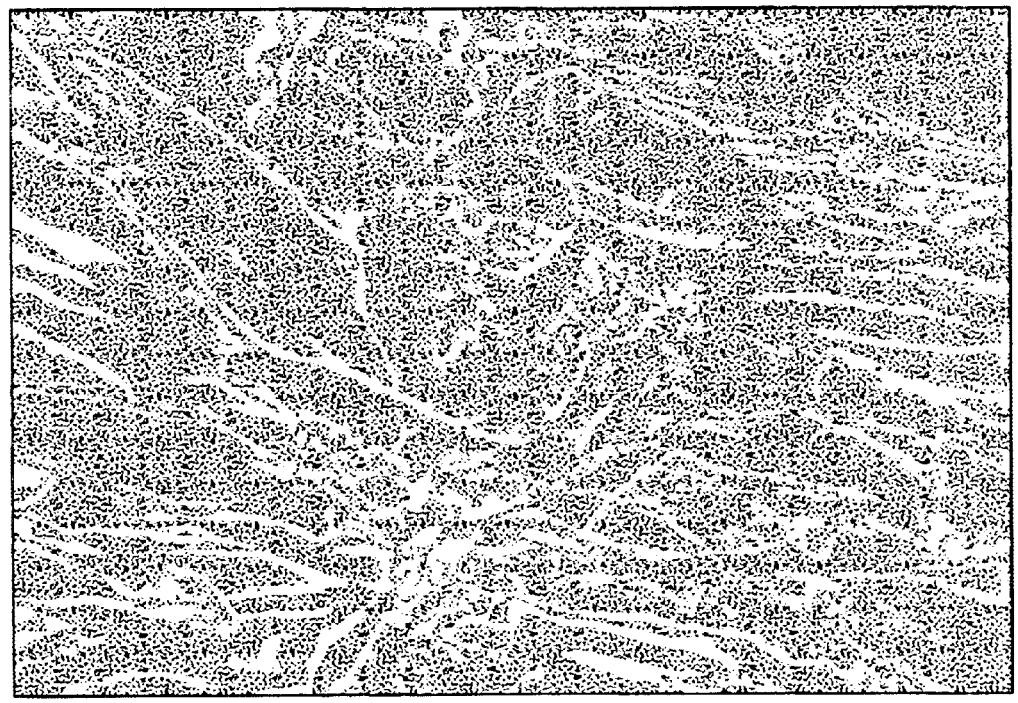

FIG. 6 illustrates a co-culture of Human foreskin fibroblasts and a non-cell seeded, FCS pre-treated CMC heparin film incubated for 7 days. This photomicrograph demonstrates that the cells remain viable and adherent to the plastic, providing evidence that the cell detachment shown in FIG. 5e is not the result of cellular toxicity.

EXAMPLE 1

Carboxymethyl cellulose (Blanose™, Aqualon), was dissolved as a 1% aqueous solution. EGDGE (20% w/w, Aldrich) was added and the solution mixed briefly using a magnetic stirrer. The resulting mixture was allowed to stand at 37° C. for 16 hours. Opsite IV 3000 (Smith&Nephew) polyurethane film was exposed to nitrogen plasma (1 minute; 100 W; Chamber pressure 0.1 to 0.2 mbar; using a PT7300 etcher) and promptly covered with a thin coat of EGDGE/CMC reaction mix (approx. 0.05 m/cm$^2$). An aqueous solution of heparin (10 mg/ml; 0.1 m/cm$^2$) was then sprayed on top of the CMC/EGDGE coating and the resulting material dried at 60° C. for 5 hours. The resulting films were then sterilised and stored dry.

The films were then immersed in Foetal Calf Serum (40% w/w, GIBCO) in phosphate buffer saline (PBS) for 16 hours at 37° C. The films were then washed twice with PBS and human keratinocytes suspend d in serum free Keratinocyte basal medium (KBM) supplemented with Keratinocyte growth medium (KGM) growth additives (available from Clonetics, Walkersville, Md. USA). As a control, aliquots of the suspended cells were added to the wells of a tissue culture plate (Falcon 3043 tissue culture plate). Cells adhered to the film and plate within 4 to 16 hours with a favourable level of spread and adherence after 1 to 2 days. This is illustrated in FIGS. 1 to 4. Following subsequent in vitro culture, the cells detached from the film and were released into the medium (see FIG. 5). Released cells formed clumps over the subsequent 7 day culture period. In contrast, cells added to tissue culture plastic adhered within 4 to 16 hours but remained adherent over the next 7 days (see FIG. 5a)

Cell detachment from the FCS pretreated CMC/heparin films was not a consequence of toxicity because if cells were cultured in tissue wells that contained a FCS pre-treated CMC/heparin film the cells remained adherent upon the culture plastic for the entire 7 day period (FIG. 6).

EXAMPLE 2

Preparation of Methyl Cellulose/EGDGE/Polyysine Films

Carbonate buffer, pH 11, was prepared as follows:
Solution A=10.6 g $Na_2CO_3$ in $H_2O$ (500 ml)
Solution B=8.4 g $NaHCO_3$ in $H_2O$ (500 ml)
Solution C=330 ml Solution A+170 ml Solution B adjusted to pH 11 with NaOH.

Methyl cellulose (1 g, Aldrich Chemicals) was dissolved in buffer (solution C) (100 ml, pH 11; stir for 16 hours at room temperature). A hydrophilic polyurethane (PU) sheet (IV3000, Smith & Nephew) and was treated with Corona discharge to increase its hydrophilicity (2 moters/mim, 0.3 kW, Aluminium trough electrode; Sherman Instruments). Methyl Cellulos solution (10 g) was mixed with Ethylene Glycol DiGlycidyl Ether (EGDGE, 10 µl) and the resulting solution spread on the polyurethane film using a spreading block to give a methyl cellulose/GDGE film of 18/1000 inch thick. The spreaded PU film was then heated (60° C., 1 hour). Polylysine in aqueous solution (1 mg/10 cm$^2$, Sigma) was sprayed onto the spreaded PU film and dried for 2 hours at 60° C. The films were washed twice with DMEM and twice in serum-free media (Gibco). Trypinised cells (primary human keratinocytes) were resuspended in serum-free media and added to the films. Cells began to adhere after 4 to 16 hours.

EXAMPLE 3

FCS pretreated heparinised/agarose film was prepared in place of CMC of example 1. Cells bound within 4 to 16 hours and detached within 7 days.

EXAMPLE 4

The film of example 3 was prepared substituting Fucoidin (Sigma) for the heparin.

EXAMPLE 5

The film of example 4 was prepared substituting gelatin (5 mg/ml, Sigma) for fucoidin.

What is claimed is:

1. A wound dressing comprising:
   a carrier layer having a wound-facing surface, said carrying layer comprising a polymeric material adherent to anchorage dependent cells and treated on the wound-facing surface thereof to be non-adherent to cells, said polymeric material comprising a polymer selected from a group consisting of polyhydroxyethylmethacrylic acids, cross-lined polyvinylalcohols, polyacrylic acids cross-linked with trialkylsucrose, polyvinylpyrrolidones, polyetherpolyesters, polyetherpolyamides, polyacrylamides, polyethylene oxide, polyurethanes and ethylenevinyl acetate copolymers, said surface being non-adherent to anchorage-dependent cells and having disposed thereon a biodegradable cell anchoring layer comprising a material selected from the group consisting of:
   (i) a polyanion selected from the group consisting of a heparin, an inositol phosphate, fucoidin, syndecan, betaglycan, perlecan, dextran sulphate, pentosan, mesoglycan and polyvinyl sulphate; and
   (ii) a polycation comprising a polypeptide; and
   said anchoring layer having anchored thereto mammalian cells which form a cell layer comprising a material selected from the group consisting of keratinocytes and fibroblasts.

2. The wound dressing of claim 1 wherein the carrier layer comprises a polymeric material adherent to anchorage dependent cells and treated on the wound facing surface thereof to be non-adherent to cells, said polymeric material comprising a polymer selected from a group consisting of polyhydroxyethylmethacrylic acids, cross-lined polyvinylalcohols, polyacrylic acids cross-linked with trialkylsucrose, polyvinylpyrrolidones, polyetherpolyesters, polyetherpolyamides, polycrylamides, polyethylene oxide, polyurethanes and ethylenevinyl acetate copolymers.

3. The wound dressing of claim 2 wherein the material is a cross-linked hydroxyalkyl cellulose, a cross-linked carboxyalkyl cellulose, a polyvinyl alcohol or an agarose.

4. The wound dressing of claim 1 wherein the carrier layer comprises a material adherent to anchorage dependent cells and treated on the wound facing surface thereof to be non-adherent to cells.

5. The wound dressing of claim 4 wherein the adherent material comprises a polymer selected from a group consisting of; polyhydroxyethylmethacrylic acids, cross-linked polyvinylalcohols, polyacrylic acids cross-linked with trialkylsucrose, polyvinylpyrrolidones, polyetherpolyesters, polyetherpolyamides, polycrylamides, polyethylene oxide, polyurethanes and ethylenevinyl acetate copolymers.

6. The wound dressing of claim 1 wherein the wound facing surface is treated with a phosphocholine, a silicone, a polyethylene glycol or a polytetrafluoroethylene.

7. A wound dressing according to claim 1 wherein the biodegradable cell anchoring layer comprises a polyanion moiety.

8. The wound dressing of claim 1 wherein the polyanion moiety has anchored thereto a cell adhesion protein.

9. The wound dressing of claim 7 wherein the polyanion is a heparin, an inositol phosphate, fucoidin, syndecan, betaglycan, perlecan, dextran sulphate, pentosan, mesoglycan or polyvinyl sulphate, and wherein said cell anchoring layer has anchored thereto mammalian cells which form a cell layer comprising either keratinocytes or fibroblasts.

10. The wound dressing of claim 1 wherein the biodegradable cell anchoring layer comprises a polypeptide.

11. The wound dressing of claim 1 wherein the polypeptide is polylysine.

12. The wound dressing of claim 1 wherein the cell layer comprises both keratinocytes and fibroblasts.

13. The wound dressing of claim 1 wherein the cell layer comprises either autologous cells or allogenic cells.

14. The wound dressing of claim 1 wherein the cell layer comprises both autologous and allogenic cells.

15. A cell culture system comprising:
  (a) a wound dressing comprising a carrier layer having a wound-facing surface, said carrier layer comprising a polymeric material adherent to anchorage dependent cells and treated on the wound-facing surface thereof to be non-adherent to cells, said polymeric material comprising a polymer selected from a group consisting of polyhydroxyethylmethacrylic acids, cross-lined polyvinylalcohols, polyacrylic acids cross-linked with trialkylsucrose, polyvinylpyrrolidones, polyetherpolyesters, polyetherpolyamides, polyacrylamides, polyethylene oxide, polyurethanes and ethylenevinyl acetate copolymers, said surface being non-adherent to anchorage dependent cells and having disposed thereon a biodegradable cell anchoring layer comprising a material selected from the group consisting of:
    (i) a polyanion selected from the group consisting of a heparin, an inositol phosphate, fucoidin, syndecan, betaglycan, perlecan, dextran sulphate, pentosan, mesoglycan and polyvinyl sulphate; and
    (ii) a polycation comprising a polypeptide; and
  (b) a vessel having interior and exterior surfaces for containing a liquid culture medium for culturing cells and the dressing.

16. A method of treating a skin trauma site on a mammalian patient comprising the step of applying to a patient a wound dressing, said dressing comprises:
  (a) a carrier layer comprising a polymeric material adherent to anchorage dependent cells and treated on a wound-facing surface thereof to be non-adherent to cells, said polymeric material comprising a polymer selected from a group consisting of polyhydroxyethylmethacrylic acids, cross-lined polyvinylalcohols, polyacrylic acids cross-linked with trialkylsucrose, polyvinylpyrrolidones, polyetherpolyesters, polyetherpolyamides, polyacrylamides, polyethylene oxide, polyurethanes and ethylenevinyl acetate copolymers, said wound-facing surface being non-adherent to anchorage dependent cells and having disposed thereon a biodegradable cell anchoring layer comprising a material selected from the group consisting of:
    (i) a polyanion selected from the group consisting of a heparin, an inositol phosphate, fucoidin, syndecan, betaglycan, perlecan, dextran sulphate, pentosan, mesoglycan and polyvinyl sulphate; and
    (ii) a polycation comprising a polypeptide; and
  (b) a layer of mammalian cells comprising a material selected from the group consisting of keratinocytes and fibroblasts anchored to the anchoring layer.

17. A method of preparing a wound dressing comprising the steps of:
  (a) obtaining a surface which is non-adherent to the anchorage dependent cells on a wound facing surface of a carrier layer which comprises a polymeric material adherent to anchorage dependent cells and treated on the wound-facing surface thereof to be non-adherent to cells, said polymeric material comprising a polymer selected from a group consisting of polyhydroxyethylmethacrylic acids, cross-lined polyvinylalcohols, polyacrylic acids cross-linked with trialkylsucrose, polyvinylpyrrolidones, polyetherpolyesters, polyetherpolyamides, polyacrylamides, polyethylene oxide, polyurethanes and ethylenevinyl acetate copolymers;
  (b) forming a biodegradable cell anchoring layer on a non-adherent to anchorage dependent cells surface of a carrier layer, said anchoring layer comprising a material selected from the group consisting of:
    (i) a polyanion selected from the group consisting of a heparin, an inositol phosphate, fucoidin, syndecan, betaglycan, perlecan, dextran sulphate, pentosan, mesoglycan and polyvinyl sulphate; and
    (ii) a polycation comprising a polypeptide; and
  (c) culturing a carrier layer which comprises a non-adherent to anchorage dependent cell surface and biodegradable cell anchoring layer in the presence of mammalian cells comprising a material selected from the group consisting of keratinocytes and fibroblasts.

\* \* \* \* \*